United States Patent
Kang et al.

(10) Patent No.: US 11,801,371 B2
(45) Date of Patent: Oct. 31, 2023

(54) MICRONEEDLE DEVICE

(71) Applicant: NATIONAL UNIVERSITY OF SINGAPORE, Singapore (SG)

(72) Inventors: Lifeng Kang, Singapore (SG); Yuanyuan Sun, Singapore (SG); Duc-Viet Nguyen, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/490,854

(22) PCT Filed: Mar. 1, 2018

(86) PCT No.: PCT/SG2018/050096
§ 371 (c)(1),
(2) Date: Sep. 3, 2019

(87) PCT Pub. No.: WO2018/160140
PCT Pub. Date: Sep. 7, 2018

(65) Prior Publication Data
US 2020/0121900 A1 Apr. 23, 2020

(30) Foreign Application Priority Data
Mar. 1, 2017 (SG) .......................... 10201701636U (51) Int. Cl.
*A61M 37/00* (2006.01)
(52) U.S. Cl.
CPC . *A61M 37/0015* (2013.01); *A61M 2037/0023* (2013.01); *A61M 2037/0046* (2013.01); *A61M 2037/0053* (2013.01)

(58) Field of Classification Search
CPC ...... A61M 37/0015; A61M 2037/0023; A61M 2037/0046; A61M 2037/0053
USPC ........................................................ 604/264
See application file for complete search history.

(56) References Cited

U.S. PATENT DOCUMENTS

| | | | |
|---|---|---|---|
| 7,588,825 | B2 | 9/2009 | Bell et al. |
| 10,828,478 | B2 | 11/2020 | McAllister et al. |
| 11,291,816 | B2 | 4/2022 | Tadros et al. |
| 2001/0020151 | A1 | 9/2001 | Reed et al. |

(Continued)

FOREIGN PATENT DOCUMENTS

| CN | 204890943 U | 12/2015 |
|---|---|---|
| CN | 105797266 A | 7/2016 |
| CN | 106232159 A | 12/2016 |

(Continued)

OTHER PUBLICATIONS

First Office Action and its English translation of the corresponding Chinese Patent Application No. 201880028954.X dated Apr. 1, 2021; 25 pages.

(Continued)

*Primary Examiner* — Phillip A Gray
(74) *Attorney, Agent, or Firm* — Harness, Dickey & Pierce, P.L.C.

(57) ABSTRACT

There is provided a microneedle device comprising a substrate and a plurality of microneedles projecting from the substrate, the substrate being substantially spherical and wherein in use, the microneedle device has three-dimensional movement. There is also provided a method of forming the microneedle device of the present invention.

20 Claims, 5 Drawing Sheets

Figure 2

(56) References Cited

U.S. PATENT DOCUMENTS

2013/0165772 A1* 6/2013 Traverso .............. A61M 5/007
600/431
2022/0226626 A1 7/2022 Tadros et al.

FOREIGN PATENT DOCUMENTS

| | | |
|---|---|---|
| GB | 2503651 A | 1/2014 |
| GB | 2503651 A1 | 1/2014 |
| JP | 2004526486 A | 9/2004 |
| JP | 2007510464 A | 4/2007 |
| JP | 2016509964 A | 4/2016 |
| WO | WO-2013101908 A1 | 7/2013 |
| WO | 2014126834 A2 | 8/2014 |
| WO | WO-2015168648 A1 | 11/2015 |
| WO | 2016170346 A1 | 10/2016 |
| WO | WO-2017151745 A1 | 9/2017 |

OTHER PUBLICATIONS

First Office Action and its English translation of the corresponding Japanese Patent Application No. 2019-548065 dated Sep. 27, 2021; 9 pages.

Mitra Mosharraf et al.; "Strategies to overcome challenges can deliver advantages over a monotherapy"; Coformulation Development of Biologics in Combination Drugs—AAPS Newsmagazine; Cover Articles; Aug. 2019; https://www.aapsnewsmagazine.org/aapsnewsmagazine/articles/2019/aug19/cover-story-aug19; 1 page.

Veeren M. Chauhan et al.; "Advancements in the co-formulation of biologic therapeutics"; Journal of Controlled Release 327; Aug. 2020; pp. 397-405.

Second Office Action dated Aug. 2, 2022, for Japanese Application No. 2019-548065; 5 pages.

Lim, S. H., et al,. "Three-dimensional printing of a microneedle array on personalized curved surfaces for dual-pronged treatment of trigger finger", Biofabrication, Jan. 10, 2017, vol. 9, pp. 1-13 [Retrieved on May 11, 2018] <DOI: 10.1088/1758-5090/9/1/015010>.

Traverso, G., et al., "Microneedles for Drug Delivery via the Gastrointestinal Tract", Journal of Pharmaceutical Sciences, Sep. 22, 2014, vol. 104, No. 2, pp. 362-367 [Retrieved on May 11, 2018] <DOI: 10.1002/JPS.24182>.

International Search Report and Writen Opinion of the International Searching Authority issued in PCT/SG2018/050096, dated May 16, 2018; ISA/SG.

* cited by examiner

Figure 4B 3D printed thorny sphere    or

STEP 3:
Applied GelMA on PDMS mould × 2

STEP 1:
PDMS casting

STEP 4:
UV curing and Store at 4°C

STEP 2:
Peeling off or    GelMA microneedle granule

MICRONEEDLE DEVICE

CROSS REFERENCE TO RELATED APPLICATIONS

This application is a U.S. National Phase Application under 35 U.S.C. 371 of International Application No. PCT/SG2018/050096 filed on Mar. 1, 2018, which claims the benefit of priority from Singapore Patent Application No. 10201701636U filed Mar. 1, 2017. The entire disclosures of all of the above applications are incorporated herein by reference.

TECHNICAL FIELD

The present invention relates to a microneedle device and a method for forming the same. In particular, the microneedle device may be suitable for penetrating skin and/or tissue.

BACKGROUND

Transdermal delivery of therapeutic and cosmetic agents offers many advantages over oral and injection routes: (i) bypass of first-pass metabolism and gastrointestinal reaction, (ii) non-invasiveness and (iii) self-administration. However, the transdermal route is often limited by the skin barrier, mainly stratum corneum, which only allows significant penetration of low molecular weight substances (<500 Da) with suitable lipophilicity. Delivery of large molecular weight drugs, such as macromolecules, peptides, insulin, vaccine, etc. via skin are challenging and most topical pharmaceutical or cosmetic products are subject to the same limitation. To overcome the skin barrier, microneedles have been developed to create micro size pathways on the skin which allow a broad spectrum of molecular drugs to enter and reach blood stream.

Conventional microneedle devices include the microneedle patch, microneedle stamp and derma roller. These devices have been proven to enhance skin permeation of therapeutic and cosmetic agents, and broadly applied in pharmaceutical and cosmetic areas. However, microneedle patch and microneedle stamp can only be applied on a flat surface and on certain skin areas which may lead to incomplete insertion, as well as inefficient drug delivery. The derma roller may be applied on a curved skin surface but its movement is limited in a one-dimensional rolling direction and on certain skin surfaces. For example, the derma roller is difficult to be applied on the eyelids. Further, the derma roller is also prone to infection due to needle reuse.

There is therefore a need for an improved microneedle device which is safe and easy to use on all skin surfaces.

SUMMARY OF THE INVENTION

The present invention seeks to address these problems, and/or to provide an improved microneedle device.

In general terms, the invention relates to a microneedle device resembling thorny substantially spherical particles with spikes of a micro size. The microneedle device of the present invention may have high skin penetration efficiency which may be able to roll easily and penetrate human skin. Accordingly, the microneedle device may be used easily on skin without limitation on the skin surface, skin condition or even the direction of movement of the microneedle device. The microneedle device may also be kept sterile by being packed separately and subsequently disposed after use to reduce any risk of infection. In view of the above, the microneedle device may be used in the transdermal delivery of drugs and/or cosmetics, or the microneedle device may be used for creating micro-channels within the skin before or after drugs and/or cosmetics are applied on the skin.

According to a first aspect, the present invention provides a microneedle device comprising a substrate and a plurality of microneedles projecting from the substrate, wherein the substrate is substantially spherical and wherein in use, the microneedle device has three-dimensional movement.

The microneedle device may be for penetrating skin or tissue. In particular, the microneedle device may be for transdermal delivery or oral delivery of a therapeutic agent or a cosmetic agent.

The microneedle device may be made of any suitable material. For example, the microneedle device may comprise gelatin, gelatin methacrylate hydrogel, hyaluronic acid, silicone, polymer, sugar, glass, ceramic and/or metal. In particular, the gelatin and/or gelatin methacrylate hydrogel may comprise gelatin derived from: porcine, bovine, fish sources, or a combination thereof.

The microneedle device may further comprise suitable additives. For example, the additive may be a hydrogel strengthening additive. In particular, the additive may be calcium phosphate, calcium carbonate, silica, graphene, carbon nanotubes, or a combination thereof.

According to a particular aspect, the microneedle device may be a disposable microneedle device. Accordingly, the microneedle device may be suitable for single-use only.

The microneedle device may comprise a therapeutic or cosmetic agent. Any suitable therapeutic and/or cosmetic agent may be used for the purposes of the present invention. For example, the therapeutic agent may be, but not limited to a drug, and the cosmetic agent may be, but not limited to, essential oils, essence, and the like. In particular, the therapeutic agent may be a transdermal delivered drug.

According to a particular aspect, the therapeutic or cosmetic agent is comprised in the microneedle device may be of any suitable form. For example, the therapeutic or cosmetic agent may be in the form of a coating on the microneedle device.

The microneedle device may have any suitable dimensions. For example, the average diameter of the substrate may be 0.05-100 mm. In particular, the average diameter may be 0.1-90 mm, 0.5-85 mm, 1-80 mm, 5-75 mm, 10-70 mm, 15-65 mm, 20-60 mm, 25-55 mm, 30-50 mm, 35-45 mm. Even more in particular, the diameter of the substrate may be 0.05-10 mm.

The microneedle device may have suitable sized and shaped microneedles. According to a particular aspect, each of the plurality of microneedles comprised in the microneedle device may have the same or different height. For example, the average height of each of the plurality of microneedles may be 10-3000 μm. In particular, the height of each of the plurality of microneedles may be 50-2800 μm, 100-2500 μm, 150-2200 μm, 200-2000 μm, 250-1800 μm, 300-1500 μm, 350-1200 μm, 400-1100 μm, 450-1000 μm, 500-950 μm, 550-900 μm, 600-850 μm, 650-800 μm, 700-750 μm. Even more in particular, the height may be 50-500 μm.

Each of the plurality of microneedles may have the same or different shape. According to a particular aspect, each of the plurality of microneedles may be a conical or pyramidal.

The present invention also provides a capsule for oral administration comprising the microneedle device according to the first aspect. The capsule may be any suitable capsule. For example, the capsule may be an enteric capsule.

According to a third aspect, the present invention provides a method of forming the microneedle device of the first aspect. The method may comprise 3D printing the microneedle device from suitable material. Alternatively, the method may comprise:
- providing a 3D printed mould of the microneedle device, wherein the mould is substantially spherical and comprises a plurality of protrusions projecting from the mould;
- casting the mould with a precursor solution; and
- curing the hydrogel precursor solution to form the microneedle device.

According to a particular aspect, the precursor solution may be a hydrogel precursor solution. In particular, the precursor solution may comprise a gelatin methacrylate hydrogel precursor solution and a photoinitiator. Any suitable photoinitiator may be used for the purposes of the present invention.

The gelatin methacrylate hydrogel precursor solution may comprise gelatin derived from any suitable source. In particular, the gelatin may be derived from: porcine, bovine, fish sources, or a combination thereof.

The hydrogel precursor solution may further comprise a suitable additive. For example, the additive may be a hydrogel strengthening additive. In particular, the additive may be calcium phosphate, calcium carbonate, silica, graphene, carbon nanotubes, or a combination thereof.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings. In the drawings:

FIG. 2(a) shows a microneedle device with triangular base pyramid shaped microneedles, FIG. 2(b) shows a microneedle device with square base pyramid shaped microneedles, FIG. 2(c) shows a microneedle device with conical shape microneedles and FIG. 2(d) shows a nearly spherical microneedle device with square based pyramid shaped microneedles;

FIGS. 7A and B show the microneedle device before insertion with sulforhodamine B (0.2% w/v) stained on the microneedle device surface, FIGS. 7C and D show the fluorescence micrographs of the human cadaver skin after a single rolling, showing the delivery of the coated sulforhodamine B and FIG. 7E shows a GelMA microneedle patch after being peeled off a PDMS mould with the inset showing the skin puncture holes dyed with trypan blue.

DETAILED DESCRIPTION

As explained above, there is a need for an improved microneedle device.

Figure 1:
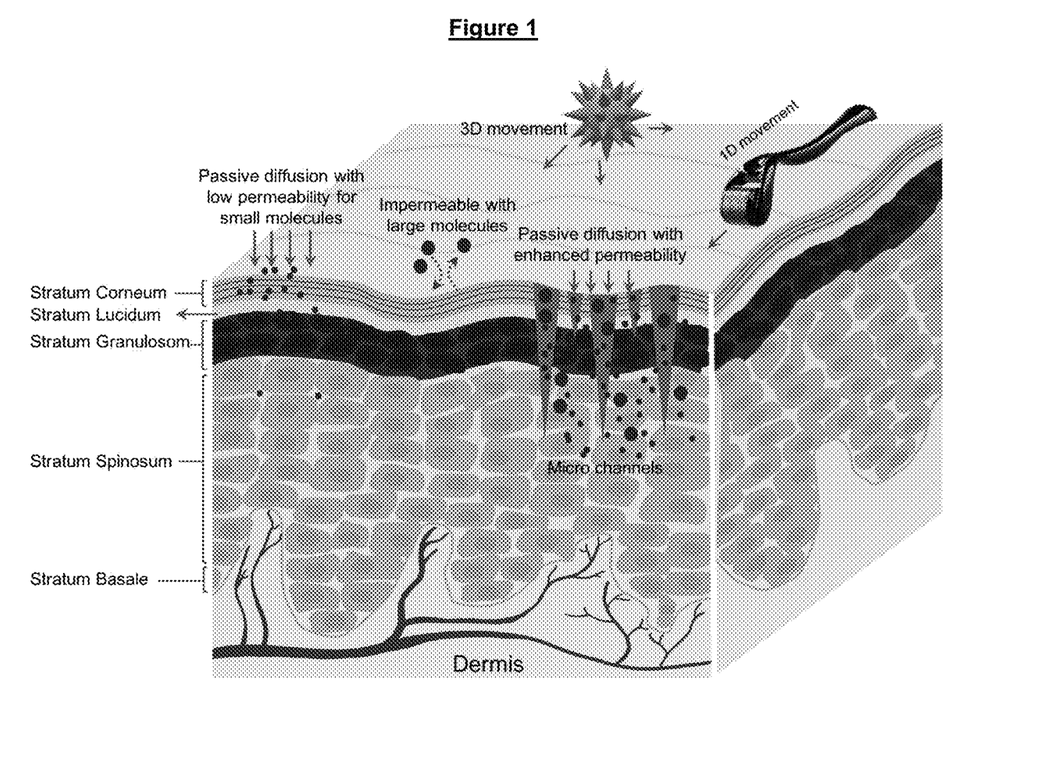
FIG. 1 shows a cross section of a skin structure onto which the microneedle device according to one embodiment of the present invention and a derma roller are applied.

The microneedle device of the present invention offers many advantages over existing microneedles. For example, the microneedle device may be used on any area or surface effectively and may be rolled on skin in any direction. This is in contrast to conventional microneedles, which are limited to be used on certain skin surfaces and areas only and allow one dimensional movement (pressing down only, as in the case of a microneedle patch or microneedle stamp) or two-dimensional movement (pressing down and rolling in one direction, as in the case of a derma roller). The microneedle device of the present invention may be pressed down and rolled in two dimensions, thereby achieving three-dimensional movement. A schematic representation of the skin structure and the movement of the microneedle device of the present invention as compared to a derma roller is shown in FIG. 1.

According to a first aspect, the present invention provides a microneedle device comprising a substrate and a plurality of microneedles projecting from the substrate, wherein the substrate is substantially spherical and wherein in use, the microneedle device has three-dimensional movement.

For the purposes of the present invention, three-dimensional movement is defined as movement in any direction on a surface, particularly a skin surface.

The substrate may be any suitable substrate. For example, the substrate may be a body which supports the microneedles projecting from it. According to a particular aspect, the substrate is substantially spherical.

For the purposes of the present invention, substantially spherical refers to a degree of deviation that is sufficiently small so as to not measurably detract from identifying the substrate as a sphere. In particular, the term substantially spherical may include a substrate which is spherical or nearly-spherical. Spherical or near-spherical may comprise substrates which are suitable for 3D printing and which have dimensions which have a low aspect ratio and avoid jagged or irregular shapes. For example, the substantially spherical substrate may have an aspect ratio which is ≤2. In particular, the aspect ratio of the substrate may be Aspect ratio may be defined as a ratio of the longest dimension of the substrate and the shortest dimension of the substrate.

The substrate may be of a suitable size. For example, the average diameter of the substrate may be 0.05-100 mm. In particular, the average diameter may be 0.1-90 mm, 0.5-85 mm, 1-80 mm, 5-75 mm, 10-70 mm, 15-65 mm, 20-60 mm, 25-55 mm, 30-50 mm, 35-45 mm. Even more in particular, the diameter of the substrate may be 0.05-10 mm.

The microneedle device may comprise any suitably sized and shaped microneedles. The microneedles may be hollow or solid microneedles. According to a particular aspect, each of the plurality of microneedles comprised in the microneedle device may have the same or different height (length). The height may be any suitable height. In particular, the height may be a suitable height so as to achieve administration of a therapeutic or cosmetic agent but at the same time short enough to avoid contacting nerves so as to reduce the possibility of pain and avoid the possibility of bleeding. The height of the microneedle also depends on the surface on which the microneedle device is to be used. For example, the average height of each of the plurality of microneedles may be 10-3000 µm. In particular, the height of each of the plurality of microneedles may be 50-2800 µm, 100-2500 µm, 150-2200 µm, 200-2000 µm, 250-1800 µm, 300-1500 µm, 350-1200 µm, 400-1100 µm, 450-1000 µm, 500-950 µm, 550-900 µm, 600-850 µm, 650-800 µm, 700-750 µm. Even more in particular, the height may be 50-500 µm.

Figure 2:
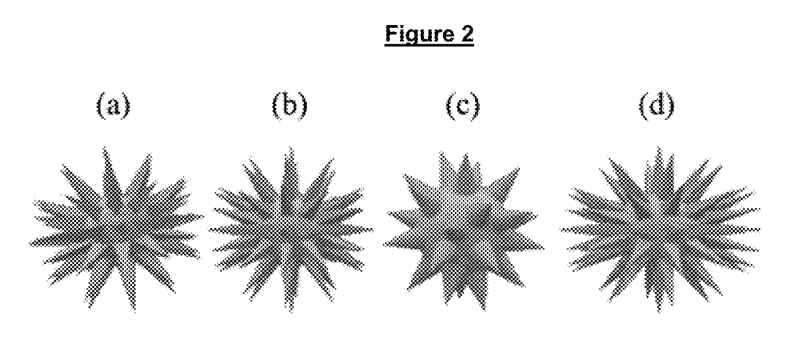
FIG. 2 shows the microneedle device of the present invention according to four embodiments.

Each of the plurality of microneedles may have the same or different shape. The plurality of microneedles projecting from the substrate may be a needle shape or a structure including a needle shape. However, for the purposes of the present invention, the microneedle may not be limited to a structure of a needle shape having a tapered tip, and may comprise a structure lacking a tapered tip. According to a particular aspect, each of the plurality of microneedles may be a conical or pyramidal. For example, each of the plurality of microneedles may have a conical shape, or a polygonal pyramid shape such as a triangular pyramid, square pyramid or in other suitable shapes. Examples of different embodiments of microneedle devices of the present invention with varied shapes are as shown in FIG. 2.

The microneedles of the microneedle device may be disposed spaced apart. For example, the microneedle device may have a suitable microneedle density. A suitable microneedle density is required to achieve efficient piercing of the skin. However, if the microneedle density is too high, maintaining the strength of the microneedles may become difficult.

The microneedle device may be made of any suitable material. For example, the microneedle device may comprise gelatin, gelatin methacrylate hydrogel, hyaluronic acid, silicone, polymer, sugar, glass, ceramic and/or metal.

The polymer may be any suitable polymer. For example, the polymer may be, but not limited to, carboxymethylcellulose (CMC) or sodium CMC, amylopectic, poly(methylmetha-acrylate) (PMMA), poly-L-lactic acid (PLA), polyglycolic acid (PGA), polylactic-co-glycolic acid (PLGA), cyclic-olefin polymer, poly(vinyl pyrrolidone) (PVP), polyethylene glycol diacrylate (PEGDA), or polyethylene glycol (PEG)-fibrinogen hydrogel.

The sugar may be, but not limited to, galactose, maltose, or dextrin.

The metal may be, but not limited to, stainless steel, titanium, palladium, palladium-cobalt alloys, or nickel.

For the purposes of the present invention, gelatin methacrylate (GelMA) hydrogel (gelatin methacryloyl) refers to a gelatin derived hydrogel comprising a majority of methacrylamide groups and a minority of methacrylate groups. GelMA is advantageous because it is less antigenic due to the natural property of gelatin. Further, GelMA is biocompatible, biodegradable, non-toxic and non-immunogenic, making it a safe material for use in contacting the human skin. Another advantage is that since GelMA is derived from gelatin and is therefore rich in gelatin source for skin collagen replacement, the microneedle device comprising GelMA may be used as an anti-aging agent and safe for drug delivery.

According to a particular aspect, the gelatin comprised in the gelatin and/or gelatin methacrylate hydrogel may be derived from: porcine, bovine, fish sources, or a combination thereof. In particular, the gelatin may be derived from porcine or fish sources. Even more in particular, the gelatin was derived from porcine or fish skin.

The microneedle device may comprise suitable additives. In particular, the gelatin, gelatin methacrylate hydrogel, hyaluronic acid and/or polymer may comprise additives.

Even more in particular, the gelatin methacrylate hydrogel may comprise suitable additives. For example, the additive may be a hydrogel strengthening additive. In particular, the additive may be calcium phosphate, calcium carbonate, silica, graphene, carbon nanotubes, or a combination thereof.

According to a particular aspect, the microneedle device may be a disposable microneedle device. Accordingly, the microneedle device may be suitable for single-use only. In this way, there is not issue of improper cleaning after use and therefore the microneedle device would eliminate any risk of contamination and infection. The sterility of the microneedle device may also be maintained.

The microneedle device may be for penetrating skin or tissue. In particular, the microneedle device may be for transdermal delivery or oral delivery of a therapeutic agent or a cosmetic agent. Accordingly, the microneedle device may comprise a therapeutic or cosmetic agent.

For the purposes of the present invention, a therapeutic or cosmetic agent may be any substance which exerts a therapeutic or prophylactic effect in a subject to be administered. Any suitable therapeutic and/or cosmetic agent may be used for the purposes of the present invention. For example, the therapeutic agent may be, but not limited to a drug, and the cosmetic agent may be, but not limited to, essential oils, essence, and the like. In particular, the therapeutic agent may be a transdermal delivered drug.

According to a particular aspect, the therapeutic or cosmetic agent comprised in the microneedle device may be of any suitable form. For example, the therapeutic or cosmetic agent may be coated on, encapsulated into or co-formulated with the microneedle device. The coating may be formed by any suitable method. For example, the coating comprising the therapeutic or cosmetic agent may be applied on the microneedle device by, but not limited to, spray coating, dip coating, dry coating, electrostatic coating, and the like. For example, the coating may be formed on each of the plurality of microneedles of the microneedle device, only on some of the microneedles, and/or on the substrate of the microneedle device. The coating may be formed only on a tip portion of the microneedle or the entire surface of the microneedle.

Oral administration of drug is still the most preferred and easy drug administration way for doctors and patients. However, for drugs like insulin, the absorption and bioavailability may be limited by the proteases and pH environment in the gastrointestinal (GI) tract. Accordingly, these drugs require chemical modification, or require to be administrated with nanocarriers or a physical method if oral delivery of such drugs is required. According to another aspect, there is also provided a capsule for oral administration comprising the microneedle device described above. The capsule may be any suitable capsule. For example, the capsule may be an enteric capsule.

Figure 3:
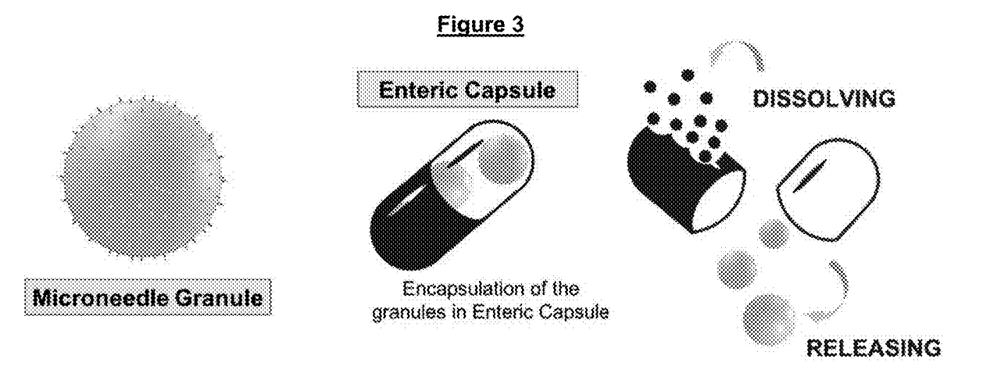
FIG. 3 shows a microneedle device encapsulated in an enteric capsule.

The microneedle device of the present invention may be suitable for oral delivery when the microneedle device comprising the drug is encapsulated within a capsule. In particular, the dimension of the microneedle device may be selected according to the diameter of the human intestine. According to a particular aspect, the capsule may comprise microneedle device formed of GelMA. As GelMA is a cellular friendly and biocompatible material derived from animal sources, the capsule comprising the microneedle device made of GelMA may be an edible and much safer device. A therapeutic agent may be incorporated into the microneedle device. The capsule, particularly the enteric capsule, would protect the microneedle device from the acidity of gastric environment. After the enteric capsule breaks down in the upper tract of the intestine, the microneedle device comprised within the enteric capsule would be released and the microneedle device would penetrate the tissue to release the therapeutic agent in certain manner. A schematic representation of the encapsulation and release of the microneedle device is shown in FIG. 3.

According to a third aspect, the present invention provides a method of forming the microneedle device as described above.

The method may comprise directly 3D printing the microneedle device. The 3D printed microneedle device may be formed from any suitable material. In particular, the method comprises polymerization of liquid monomeric acrylate compounds into solid polymeric compounds and wherein the reaction is repeated layer by layer in a bottom-up configuration.

Alternatively, the method of forming the microneedle device described above comprises:
  providing a 3D printed mould of the microneedle device, wherein the mould is substantially spherical and comprises a plurality of protrusions projecting from the mould;
  casting the mould with a precursor solution; and
  curing the precursor solution to form the microneedle device.

The providing comprises providing a suitable 3D printed mould. The 3D printed mould of the microneedle device may be of suitable dimensions. In particular, the dimensions may be selected based on the application of the microneedle device and the user of the microneedle device. In other words, the microneedle device of the present invention may be customised to a specific user.

According to a particular aspect, the precursor solution comprises a gelatin hydrogel precursor solution or a gelatin methacrylate hydrogel precursor solution. The precursor solution may further comprise a photoinitiator. Any suitable photoinitiator may be used for the purposes of the present invention. In particular, the photoinitiator may be any suitable photoinitiator which would enable cross-linking to form the hydrogel. For example, the photoinitiator may be, but not limited to, (1-[4-(2-Hydroxyethoxy)-phenyl]-2-hydroxy-2-methyl-1-propane-1-one) (i.e. Irgacure 2959), (Bis(2,4,6-trimethylbenzoyl)-phenylphosphineoxide) (i.e. Irgacure 819), or a combination thereof.

The gelatin comprised in the gelatin hydrogel precursor solution or gelatin methacrylate hydrogel precursor solution may comprise gelatin derived from any suitable source. In particular, the gelatin may be derived from: porcine, bovine, fish sources, or a combination thereof. In particular, the gelatin may be derived from porcine or fish sources. Even more in particular, the gelatin may be derived from porcine or fish skin.

The precursor solution may further comprise a suitable additive. For example, the additive may be a hydrogel strengthening additive. In particular, the additive may be calcium phosphate, calcium carbonate, silica, graphene, carbon nanotubes, or a combination thereof.

The curing of the hydrogel precursor solution to form the microneedle device may be under suitable conditions. For example, the curing may be curing under ultraviolet (UV), visible or infrared light for a pre-determined period of time. In particular, the curing may be under light of wavelength 200-850 μm. The pre-determined period of time may be at least 30 seconds. For example, the pre-determined period of time may be 2-300 minutes, 5-240 minutes, 10-200 minutes, 15-180 minutes, 30-150 minutes, 45-120 minutes, 60-100 minutes, 75-90 minutes. Even more in particular, the curing may be for about 30 minutes.

Figure 4A:
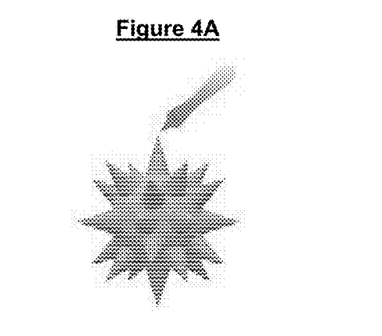
FIG. 4(A) shows a representation of a 3D printing of a microneedle device and FIG. 4(B) shows a schematic representation of a method of forming the microneedle device of the present invention according to one embodiment.
Figure 4B:
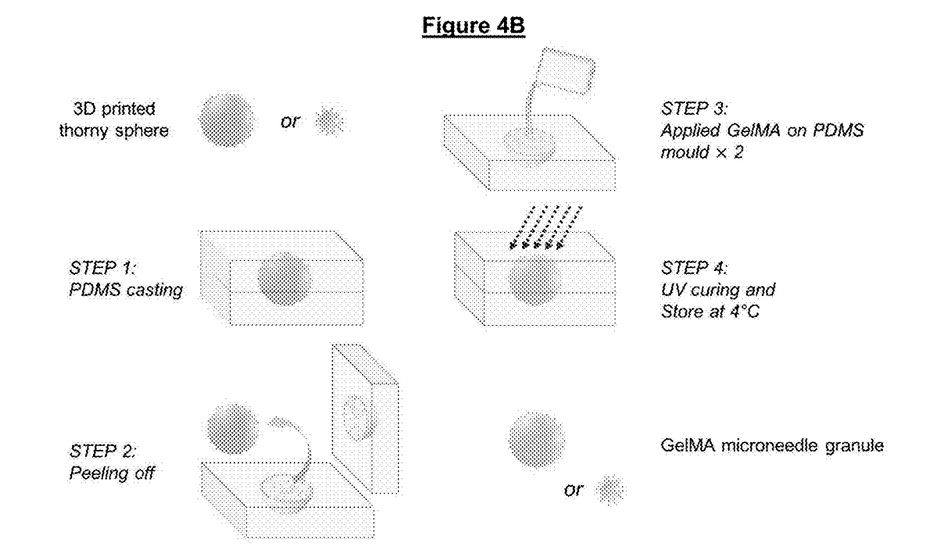

A method of forming the microneedle device of the present invention will now be described in relation to a particular embodiment. A schematic representation of the method is as shown in FIG. 4(B). A 3D printed mould is prepared using a suitable 3D printing method. The mould is then cured for a pre-determined period of time and thereafter washed with a suitable solvent such as isopropyl alcohol (IPA) or acetone before being cast in a suitable polymer, as shown as step 1 of FIG. 4(B). For example, the polymer may be polydimethylsiloxane (PDMS). The polymer-casted mould is then cured at a pre-determined temperature for a pre-determined period of time. The microneedle device mould is then peeled off (step 2 of FIG. 4(B)) from the printed moulds and filled with a hydrogel precursor solution (step 3 of FIG. 4(B)). The hydrogel precursor solution may be as described above. The precursor solution is then cured (step 4 of FIG. 4(B)) for a suitable period of time and exposed to UV light to form the microneedle device.

The methods of the present invention provide a microneedle device comprising a substrate and a plurality of microneedles projecting from the substrate. The advantage of the moulding method as shown in FIG. 4(B) is that despite the small size of the microneedles projecting from the substrate, the microneedles do not break when the microneedle device is being removed from the mould it is formed in.

Whilst the foregoing description has described exemplary embodiments, it will be understood by those skilled in the technology concerned that many variations may be made without departing from the present invention.

Having now generally described the invention, the same will be more readily understood through reference to the following examples which are provided by way of illustration, and are not intended to be limiting.

EXAMPLE

Example—Preparation and Testing of Microneedle Device

3D Printing of Microneedle Device

The microneedle device was designed to appropriate dimensions using Solidwork 2015 or 3D Builder (Microsoft) and printed using Titan 3D printer (Kudo3D Inc.). A commercial castable resin (3DM castable resin, Kudo3D Inc.) was used to 3D print the microneedle device. Other 3D printable materials, for example gelatin, gelatin methacrylate hydrogel, hyaluronic acid, silicone, polymer, sugar, glass, ceramic and/or metal may also be used with suitable 3D printers. The printing parameters were determined with reference to the "Recommended Printing Parameters: Exposure Time, Lifting Height, & Lifting Speed" guide from Kudo3D Inc. website. The Titan 3D printer worked based on Digital Light Processing which is suitable for photopolymer materials.

Figure 5:
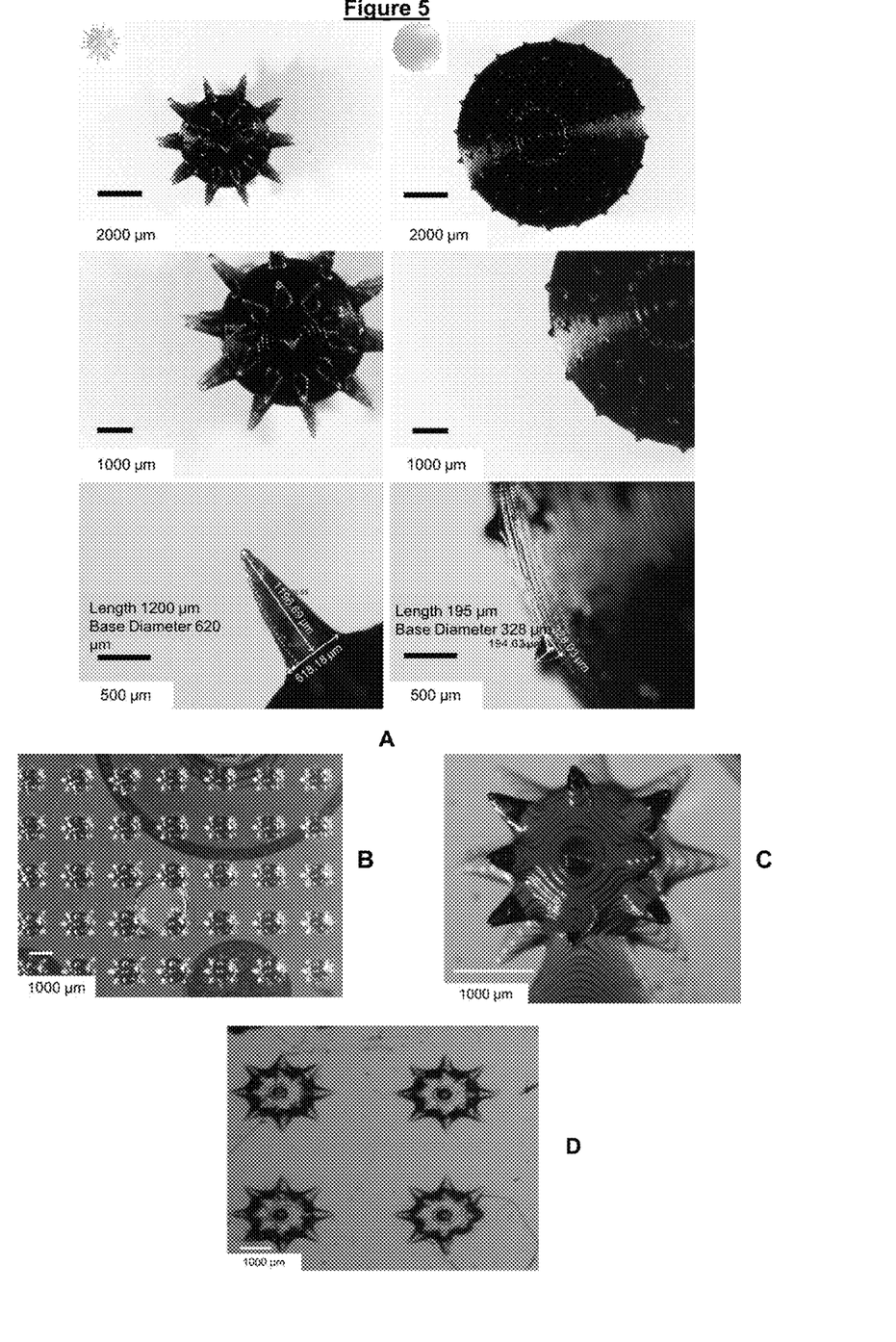
FIG. 5(A) shows images of 3D printed microneedle devices (i) and (ii)
FIG. 5(B) shows an array of printed microneedle device mould.
FIG. 5(C) shows a close-up picture of the microneedle device mould of FIG. 5(B)
FIG. 5(D) shows the PDMS moulds after peeling off the printed moulds.

The microneedle device was printed layer by layer from a liquid pool of printing materials. The printed microneedle device was rinsed with isopropyl alcohol (IPA) to remove residual resin, and post-cured in a UV chamber for 2 hours. Structure integrity of the 3D printed microneedle device was examined under SMZ1500 stereo microscope (Nikon, Japan) and the results are as shown in FIG. 5A(i) and (ii), which are two different shapes of microneedle devices formed from this method. The printed microneedle devices were then stored in dry condition and used for skin penetration study.

3D Printing of Microneedle Device Mould 3D printed microneedle device moulds were formed from the same manner as described above in relation to 3D printing of microneedle device. The size of the substrate of the 3D printed microneedle device and the dimensions of microneedles relating to the height and angle of the protrusions depend on the design parameters used using the 3D printing software.

The 3D printed moulds were printed using commercial castable resin (3DM castable resin, Kudo3D Inc.).

PDMS Mould Preparation

The 3D printed moulds were washed with isopropyl alcohol (IPA) to remove residual resin and post-cured under UV for 2 hours before casting PDMS precursor solution. PDMS-casted moulds were later cured inside an oven at 80° C. for 2 hours. The PDMS microneedle device moulds were peeled off from the printed moulds and filled by GelMA precursor solution (FIG. 4(B)). FIGS. 5A, 5B and 5C show printed microneedle devices using commercial resin, 3D printed microneedle device mould, and magnified microneedle mould, respectively. FIG. 5D shows PDMS moulds after removal of the printed moulds. It can be seen that the printed structures were completely transferred to the PDMS moulds.

GelMA Synthesis

Fish gelatin, porcine gelatin (type A, bloom strength 300), methacrylic anhydride (MA) (containing 2,000 ppm topanol A as inhibitor, 94%) and dialysis tubing (MWCO 12,400) were purchased from Sigma. GelMA synthesis was modified from the protocol described in Bulcke et al, 2000, Biomacromolecules, 1:31-38. The reaction was conducted at 50° C., using 10 g of gelatin (either from fish or porcine sources) and dissolved in 80 ml deionized (DI) water. 3.1 M sodium hydroxide was used to adjust pH of the clear gelatin solution to 9, then 6 ml of MA was added drop-wise into hot gelatin solution (at 50° C.) under vigorous stirring. After 3 hours of reaction, 200 ml of DI water was added to stop the reaction and all solution was put into a dialysis tubing dipped in plenty of hot DI water (~5 litres) for 5 days to remove the low molecular weight impurities. Water was changed every day. After dialysis, the gel solution was lyophilized for 5 days and stored in −80° C. The GelMA had a degree of methacrylation of about 70%.

Hydrogel Preparation and Subsequent Microneedle Device Synthesis

The protocol for both fish and porcine GelMA were similar except the fact that heat controller was required for pig GelMA as it solidified at room temperature. 0.5 or 1 gram of lyophilized GelMA was dissolved in 5 ml of hot DI water (50° C.) to prepare 10% or 20% GelMA solution, respectively. 0.1 gram of Irgacure 2959 was dissolved in 1 ml of 70% ethanol for 10% w/v stock solution of photoinitiator. 1% v/v of photoinitiator stock solution was later added into clear GelMA solution to form GelMA precursor solution. GelMA precursor solution was poured into the PDMS moulds and de-gassed under vacuum for 30-60 minutes. Vacuum chamber temperature was set at room temperature for fish GelMA and 50° C. for pig GelMA. The filled PDMS microneedle device moulds were then cured under UV (Omnicure) for 1-5 minutes, and subsequently put into a 4° C. fridge and enclosed within a perforated box for slow evaporation of water (FIG. 4(B)). Cold slow evaporation maintains the microneedle shape. Once the microneedle device shrunk and hardened, it was removed from the PDMS mould without breakage. Structural integrity of the prepared microneedle device was examined under SMZ1500 stereo microscope (Nikon, Japan).

Microneedle Device Prototype

Figure 6:
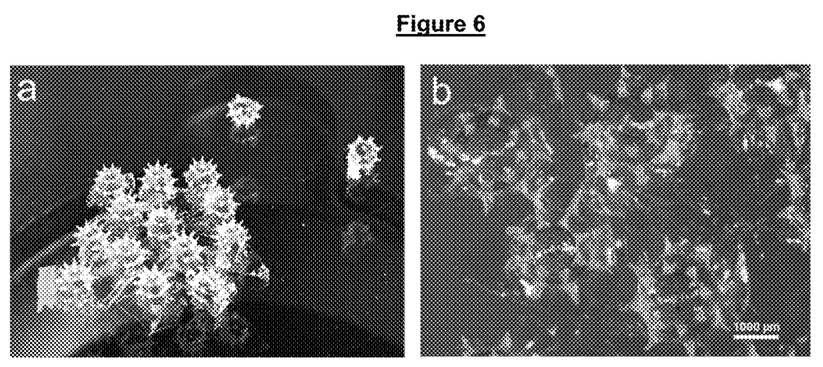
FIG. 6(a) shows a GelMA microneedle device peeled off from a PDMS mould and FIG. 6(b) shows a microneedle device under a microscope.

FIG. 6 shows GelMA microneedle device after removal from the PDMS moulds. The microneedle device shape remains that of the positive moulds with unbroken needles. The key factor to preserve structure integrity of microneedle granules after removal is cold slow evaporation to remove water content in order to stiffen the microneedle device and shrink them down to an appropriate size to be removed from the moulds.

Skin Penetration Demonstration

Figure 7:
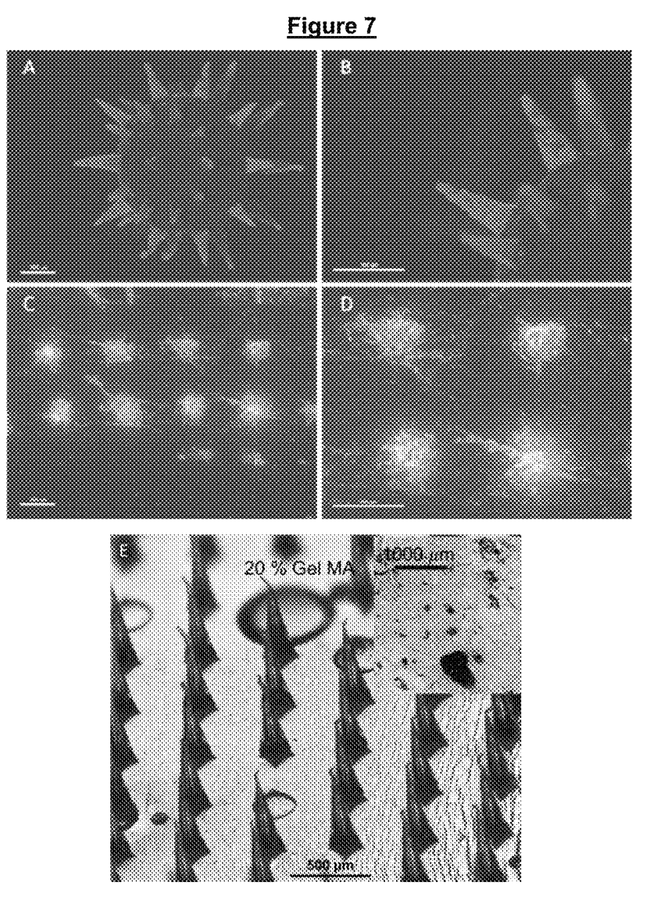
FIG. 7 shows a microneedle device staining and human cadaver skin penetration.

Human cadaver skin was donated by a 58 year old female and obtained from the Science Care (Phoenix, Ariz., USA). The use of human skin was approved by the National University of Singapore Institutional Review Board. Before commencing work on the skin, the formed microneedle device was soaked in 0.2% w/v of sulforhodamine B for 2 hours and air dried at 40° C. for 20 minutes. The coating was viewed using Nikon SMZ25 stereomicroscope under fluorescence as shown in FIGS. 7A and 7B). The resulting microneedle device was rolled on the human skin once in one direction with a gentle force applied by the thumb without breaking the needle. After cleaning the working area using ethanol, fluorescence micrograph of the skin after insertion of the microneedle device was obtained to demonstrate the delivery of the sulforhodamine B (FIGS. 7C and 7D).

A GelMA microneedle patch was also prepared to demonstrate that GelMA is suitable for transdermal delivery through skin puncture test. FIG. 7E shows a GelMA microneedle patch after peeling off from a PDMS mould, and the inset shows skin puncture holes after applying the microneedle patch on human skin cadaver. As a result, GelMA microneedle device can be used for transdermal delivery. Thus, this shows that the microneedle device of the present invention may be used in transdermal delivery.

Microneedle Device Stiffness Control

Figure 8:
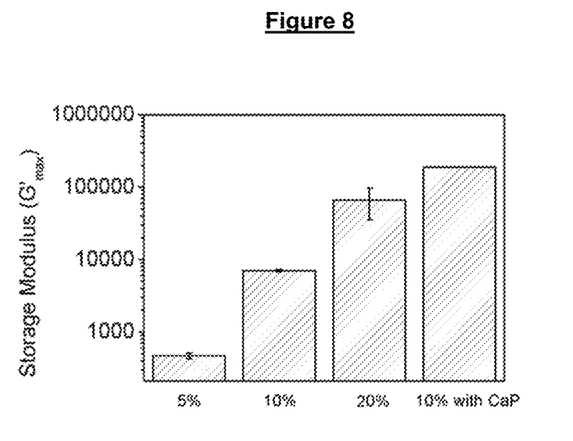
FIG. 8 shows the gel stiffness (storage modulus) of fish GelMA with varying GelMA concentrations and composition.

The storage modulus (gel stiffness) of the GelMA microneedle device was measured using Anton Paar Rheometer. Gel stiffness was greatly enhanced (by a two order magnitude for 10% GelMA) with the presence of calcium phosphate microparticles (FIG. 8). The results show that the microneedle device stiffness may be enhanced by magnitudes of up to three orders and therefore skin penetration can be well controlled.

The invention claimed is:

1. A microneedle particle comprising:
   a substrate and a plurality of microneedles projecting from the substrate, wherein the substrate is substantially spherical and wherein
   the microneedle particle is configured to move in three-dimensions and the plurality of microneedles are configured to penetrate skin or tissue when the microneedle particle is rolled on the skin or tissue in any direction,
   wherein the microneedle particle further comprises a therapeutic or cosmetic agent encapsulated into or co-formulated with the microneedle particle,
   wherein the substrate has a diameter of 0.05 millimeters to 100 millimeters, and
   wherein an average height of the plurality of microneedles is (i) 50 micrometers to 500 micrometers, or (ii) 500 micrometers to 950 micrometers.

2. The microneedle particle according to claim 1, wherein the microneedle particle comprises gelatin, gelatin methacrylate hydrogel, hyaluronic acid, silicone, polymer, sugar, glass, ceramic and/or metal.

3. The microneedle particle according to claim 1, wherein the microneedle particle comprises gelatin derived from: porcine, bovine, fish, or a combination thereof.

4. The microneedle particle according to claim 1, wherein the microneedle particle further comprises calcium phosphate, calcium carbonate, silica, graphene, carbon nanotubes or a combination thereof.

5. The microneedle particle according to claim 3, wherein the microneedle particle is biodegradable.

6. The microneedle particle according to claim 1, wherein the diameter of the substrate is 0.05 millimeters to 10 millimeters.

7. The microneedle particle according to claim 1, wherein the average height of the plurality of microneedles is 50 micrometers to 500 micrometers.

8. The microneedle particle according to claim 1, wherein each of the plurality of microneedles has the same or different shape.

9. The microneedle particle according to claim 8, wherein each of the plurality of microneedles is conical or pyramidal.

10. The microneedle particle according to claim 1, wherein the microneedle particle is configured for transdermal delivery of the therapeutic or cosmetic agent.

11. A capsule for oral administration comprising the microneedle particle according to claim 1, and wherein the capsule is an enteric capsule.

12. A method of forming a microneedle particle, the method comprising:
   providing a 3D printed mould having the shape of the microneedle particle, wherein the 3D printed mould is substantially spherical and comprises a plurality of protrusions projecting from the 3D printed mould;
   casting the 3D printed mould of the microneedle device in a polymer to form a polymer-casted mould;
   curing the polymer-casted mould to form a polymer mould;
   peeling off the polymer mould from the 3D printed mould;
   casting the polymer mould with a precursor solution;
   curing the precursor solution within the polymer mould;
   shrinking and/or hardening the cured precursor solution within the polymer mould to form the microneedle particle; and
   removing the microneedle particle from the polymer mould,
   wherein the microneedle particle comprises a substantially spherical substrate and a plurality of microneedles projecting from the substantially spherical substrate, the substantially spherical substrate has a diameter of 0.05 millimeters to 100 millimeters, and an average height of the plurality of microneedles is (i) 50 micrometers to 500 micrometers, or (ii) 500 micrometers to 950 micrometers,
   wherein the microneedle particle is configured to move in three-dimensions and the plurality of microneedles are configured to penetrate skin or tissue when the microneedle particle is rolled on the skin or tissue in any direction, and
   wherein the microneedle particle further comprises a therapeutic or cosmetic agent encapsulated in or co-formulated with the microneedle particle.

13. The method according to claim 12, further comprising:
   printing the 3D printed mould from gelatin, gelatin methacrylate hydrogel, hyaluronic acid, silicone, polymer, sugar, glass, ceramic, and/or metal.

14. The method according to claim 12, wherein the microneedle particle comprises gelatin, gelatin methacrylate hydrogel, hyaluronic acid, silicone, polymer, sugar, glass, ceramic and/or metal.

15. The method according to claim 12, wherein the precursor solution further comprises calcium phosphate, calcium carbonate, silica, graphene, carbon nanotubes, or a combination thereof.

16. The microneedle particle according to claim 1, wherein the microneedle particle is formed by 3D printing.

17. The microneedle particle according to claim 1, wherein the therapeutic or cosmetic agent is co-formulated with the microneedle particle.

18. The microneedle particle according to claim 1, wherein the plurality of microneedles are uniformly distributed over an entire surface area of the substrate.

19. The microneedle particle according to claim 1, wherein the microneedle particle is configured to deliver the therapeutic or cosmetic agent orally.

20. The microneedle particle according to claim 1, wherein the average diameter of the substrate is 0.1 millimeters to 0.5 millimeters, and wherein the average height of the plurality of microneedles is 250 micrometers to 400 micrometers.

* * * * *